United States Patent [19]

Haeckel

[11] 4,007,639
[45] Feb. 15, 1977

[54] CAPILLARY VESSEL FOR BLOOD REMOVAL

[75] Inventor: Rainer Haeckel, Hannover, Germany

[73] Assignee: Firma Walter Sarstedt Kunststoff-Spritzgusswerk, Numbrecht, Rommelsdorf, Germany

[22] Filed: Aug. 14, 1975

[21] Appl. No.: 604,812

[30] Foreign Application Priority Data

Aug. 16, 1974 Germany .......................... 2439218

[52] U.S. Cl. ............................................ 73/425.4 P
[51] Int. Cl.² ............................................ B01L 3/02
[58] Field of Search ........ 73/425.4 P, 425.6, 423 A, 73/423 R; 206/305; 23/259, 292; 128/2 F, 276

[56] References Cited

UNITED STATES PATENTS

| 2,685,800 | 8/1954 | Natelson | 73/425.4 P |
|---|---|---|---|
| 2,797,150 | 6/1957 | Righy | 23/292 |
| 3,518,164 | 6/1970 | Andelin | 23/292 |
| 3,676,076 | 7/1972 | Grady | 23/292 |
| 3,699,348 | 10/1972 | Hocherl | 73/425.6 |

FOREIGN PATENTS OR APPLICATIONS 2,203,174  8/1973  Germany .......................... 73/425.6

Primary Examiner—S. Clement Swisher
Attorney, Agent, or Firm—Browdy and Neimark

[57] ABSTRACT

A capillary vessel for blood comprises a nozzle of capillary diameter, with a remaining portion widened of size such that a micropipette can be inserted therein, the end of the nozzle being closable with a plug.

10 Claims, 4 Drawing Figures

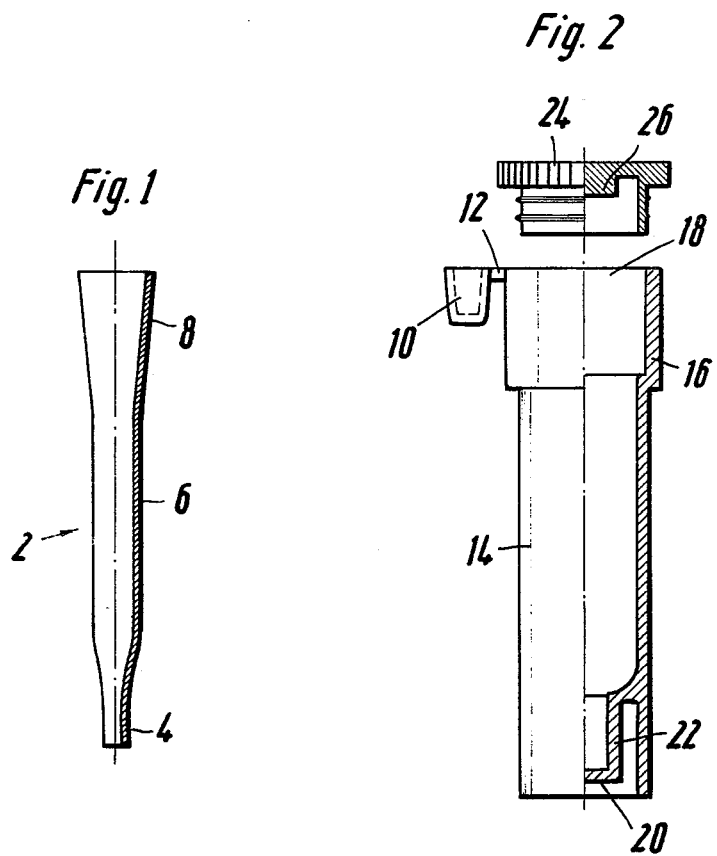
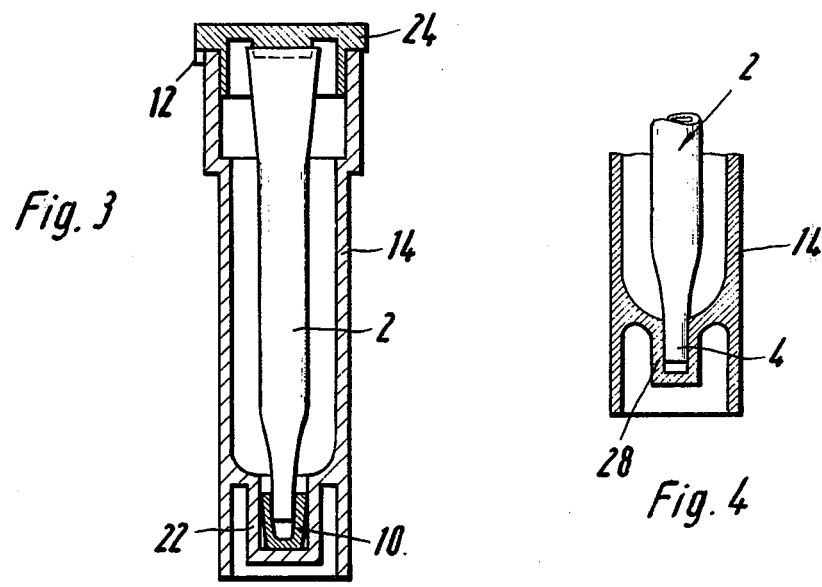

4,007,639

CAPILLARY VESSEL FOR BLOOD REMOVAL

FIELD INVENTION

The invention relates to a capillary vessel for extracting very small quantities of blood.

BACKGROUND OF THE INVENTION

In a known method of the said type, the blood is extracted from small cuts or punctures by means of small capillary tubes in which the blood automatically rises as a result of the capillary action. For the purpose of examining or treating the blood, the blood had to be blown out into a micro-container by means of the mouth or a separate blower. This method is either dangerous for the operator or can be carried out only at a relatively great expense, it also being disadvantageous that a portion of the small quantity of blood is lost.

A reservoir has already been proposed for emptying these known small capillary tubes and is characterised by a tubular body which is closed at its bottom end and whose interior space is subdivided by a partition to form a side pocket for receiving one or a plurality of small capillary tubes, and a main chamber which tapers conically downwardly and opens into a collecting pocket of circular cross section, wherein the bottom of the side pocket lies above the top edge of the collecting pocket, and the partition leaves free a communication between the side pocket and the main chamber and does not quite reach to the bottom of the side pocket. The side pocket is loaded with the small capillary tubes filled with blood and, if required, the top of the container is closed by means of a plug. Centrifuging is then carried out, wherein the blood located in the capillary tubes is centrifuged downwardly therefrom and, by way of the bottom of the side pocket and the connection between the latter and the main chamber, enters the main chamber where the blood collects in the collecting pocket. The blood or, after appropriate treatment, the serum or plasma, can be extracted from the collecting pocket by means of a micropipette.

SUMMARY OF THE INVENTION

The invention is intended to further simplify the extracting of the blood from the capillary vessels.

In accordance with the invention, this object is achieved by means of a capillary vessel which is characterized in that only the nozzle is in the form of a capillary tube, while the remaining region is widened such that a micropipette can be inserted, and that at least the end of the nozzle is closable by means of a plug.

Like the known small capillary tubes, the capillary vessel in accordance with the invention is automatically filled with blood when it is applied to a cut or puncture. Satisfactory results are obtained if the nozzle, in the form of a capillary tube, has a length of approximately 2 to 5 mm. The region of the capillary vessel contiguous to the nozzle can be of substantially cylindrical construction, the volume being sufficiently large to accommodate approximately 300 microlitres which are normally required for examination of the blood.

The blood can be extracted directly from the capillary vessel in accordance with the invention by means of a micropipette. It is also possible to centrifuge the blood directly in the capillary vessel, according to requirements, before the blood is extracted therefrom, and to subsequently extract the plasma or serum produced from the capillary vessel.

To facilitate the inserting of the pipette, the end remote from the nozzle may be widened in a trumpet-shaped manner.

Preferably, the plug for sealing the nozzle is in the form of a slip-on cap of plastics material and prevents the blood from being forced out of the capillary vessel upon introducing the pipette or during centrifuging.

Alternatively, according to use, the end remote from the nozzle may be sealed. For this purpose, there may be provided a substantially cylindrical outer vessel which is adapted to the length of the capillary vessel and which has an access opening at one end, the access opening being closable by means of a press-in cover which at the same time closes the capillary vessel inserted into the outer vessel. The press-in cover can have a plug-shaped, inwardly projecting central portion which engages into the trumpet-shaped opening of the capillary vessel.

Advantageously, the closed end of the outer vessel has a substantially cylindrical receiving pocket whose diameter corresponds to the external diameter of the cap for sealing the nozzle of the capillary vessel. By virtue of this feature, the capillary vessel can be fixed centrally in a sealed manner within the outer vessel.

The closure cap and/or the press-in cover may be made from the same material as the outer vessel and each may be integrally connected to the outer vessel by means of a frangible connection. In this manner, the outer vessel may be manufactured in one operation together with the closure cap and the press-in cover, from, for example, plastics material by the injection-moulding method, there being at the same time the advantage that, when the device is put into use, the user has easy access to all the parts which have to be removed from the outer vessel merely by breaking the frangible connections.

An alternative embodiment of the invention resides in dispensing with a separate cap for closing the nozzle of the capillary vessel. In this instance, the closed end of the outer vessel may have a cap-shaped bulge whose internal cross section is adapted to the external cross section of the nozzle of the capillary vessel. The capillary vessel is then automatically closed when in its inserted state and can be manipulated in the same manner as in the first embodiment.

BRIEF DESCRIPTION OF DRAWING

The invention is illustrated in the drawings by way of example and will be described in detail hereinafter with reference to the drawings, in which:

FIG. 1 shows an embodiment of the capillary vessel drawn to an enlarged scale, the left-hand side being shown in elevation and the right-hand side being shown in section;

FIG. 2 shows an embodiment of the outer vessel including the closure cap and the press-in cover, also drawn to an enlarged scale, the left-hand side being shown in elevation and the right-hand side being shown in section;

FIG. 3 is a section through the outer vessel with the capillary vessel inserted therein, and FIG. 4 is the same section as shown in FIG. 3 through the bottom portion of a different embodiment of the outer vessel.

DETAILED DESCRIPTION OF EMBODIMENTS

In the capillary vessel 2 shown in FIG. 1, the nozzle 4 for applying to the cut has approximately the same dimensions as the known, continuously cylindrical small capillary tubes. The length of the nozzle 4 need only be approximately 2 to 5 mm. A widened cylindrical region 6, having a volume of approximately 300 microliters, is contiguous to the nozzle 4. The end 8 remote from the nozzle is widened in a trumpet-shaped manner, so that a conventional micropipette can be conveniently inserted into the capillary vessel and the contents of the capillary vessel can be removed by pipetting.

A cap 10 of plastics material is provided for closing the nozzle 4 and, as shown in FIG. 2, is integrally connected to the outer vessel 14 by means of a frangible connection 12, the frangible connection 12 having to be broken away in order to use the closure cap 10. The substantially cylindrical outer vessel 14 has an access opening 18 at its top end 16, while the bottom end 20 is closed and is in the form of a cylindrical receiving pocket 22 whose diameter corresponds approximately to the largest external diameter of the closure cap 10.

The closure cap 10 is of conical construction and, consequently, can be conveniently inserted into the receiving pocket 22 of the outer vessel 14 together with the capillary vessel 2. The capillary vessel 2 is thereby centred in the outer vessel 14 and secured in its upright position.

The access opening 18 of the outer vessel 14 is closed by means of a press-in cover 24 which may either be provided separately or, like the closure cap 10, may be injection-moulded to the outer vessel 14 by way of a frangible connection. The press-in cover 24 at the same time closes the top end of the capillary vessel 2. For this purpose, the inside of the cover 24 may be provided with a plug-shaped, inwardly projecting central portion 26 which engages with a close-tolerance fit into the top, trumpet-shaped widened end 8 of the capillary vessel 2 and tightly seals the latter.

Referring to FIG. 3, the capillary vessel 2, when in the inserted state, is hermetically sealed and at the same time packed in the outer vessel 14 so as to be protected against impacts and jolts. In this closed state, the capillary vessel 2 and its contents can be transported without problems. In this arrangement, the blood can also be centrifuged in the capillary vessel without a separate reservoir having to be provided for this purpose.

In the embodiment illustrated in FIG. 4, in which the individual parts are provided with the same reference numerals as in the first embodiment, a separate closure cap is not provided for the nozzle 4 of the capillary vessel 2, the corresponding closure being integrally formed with the outer vessel 14. For this purpose, the closed end of the outer vessel 14 has a cap-shaped bulge 28 whose internal cross section has the same configuration as the closure cap 10 described in conjunction with the first embodiment. In this case, the capillary vessel 2, after it has been filled with blood, is inserted directly into the outer vessel 14, the nozzle being automatically closed by the cap-shaped bulge 28 into which it is inserted. The outer vessel 14 and the cover 24 can be of the same construction as in the embodiment shown in FIGS. 2 and 3 without, however, an additional closure cap 10 being injection-moulded on the outside of the outer vessel 14.

What is claimed is:

1. Capillary vessel for extracting very small quantities of blood, wherein the nozzle is in the form of a capillary tube, while the remaining region is widened such that a micropipette can be inserted therein, and at least the end of the nozzle is closable by means of a plug.

2. Capillary vessel as claimed in claim 1, wherein nozzle in the form of a capillary tube has a length of approximately 2 to 5 mm.

3. Capillary vessel as claimed in claim 1, wherein the region contiguous to the nozzle is of substantially cylindrical construction and has a volume of approximately 300 microliters.

4. Capillary vessel as claimed in claim 3, wherein the end remote from the nozzle is widened in a trumpet-shaped manner.

5. Capillary vessel as claimed in claim 1, wherein the plug for closing the nozzle is in the form of a plastic slip-on cap.

6. Capillary vessel as claimed in claim 1, wherein a substantially cylindrical outer vessel is provided for closing the end remote from the nozzle, which outer vessel is adapted to the length of the capillary vessel and has an access opening at one end, and the access opening is closable by means of a press-in cover which at the same time closes the capillary vessel inserted into the outer vessel.

7. Capillary vessel as claimed in Claim 6, wherein the press-in cover has a plug-shaped, inwardly projecting central portion which engages into the opening of the capillary vessel which is trumpet-shaped.

8. Capillary vessel as claimed in claim 6 wherein the outer vessel has at its closed end a substantially cylindrical receiving pocket whose diameter corresponds approximately to the external diameter of the closure cap.

9. Capillary vessel as claimed in claim 8, wherein the press-in cover is made from the same material as the outer vessel and is integrally connected to the outer vessel by means of a frangible connection.

10. Capillary vessel as claimed in claim 6, wherein the closed end of the outer vessel has a cap-shaped bulge whose internal cross section is adapted to the external cross section of the nozzle of the capillary vessel.

* * * * *